United States Patent [19]

Parrish et al.

[11] Patent Number: 4,799,966
[45] Date of Patent: Jan. 24, 1989

[54] PROCESS FOR CONVERTING ALPHA TO BETA-LACTOSE

[75] Inventors: Frederick W. Parrish, Metairie, La.; Samuel Serota, Philadelphia, Pa.

[73] Assignee: The United States of America as represented by the Secretary of Agriculture, Washington, D.C.

[21] Appl. No.: 63,358

[22] Filed: Jun. 18, 1987

[51] Int. Cl.$^4$ .................. C13F 1/00; C13F 1/02; C13K 5/00
[52] U.S. Cl. .................. 127/63; 127/58; 127/61; 127/31
[58] Field of Search .................. 127/58, 63, 31, 61

[56] References Cited

U.S. PATENT DOCUMENTS

| | | | |
|---|---|---|---|
| 1,956,811 | 5/1934 | Sharp | 127/31 |
| 2,182,619 | 12/1939 | Sharp et al. | 127/31 |
| 2,319,562 | 5/1943 | Sharp | 127/31 |
| 2,710,808 | 6/1955 | Peebles et al. | 127/31 |
| 4,349,542 | 9/1982 | Staniforth | 127/31 |

FOREIGN PATENT DOCUMENTS

| | | | |
|---|---|---|---|
| 0124928 | 11/1984 | European Pat. Off. | 127/63 |
| 1146199 | 7/1986 | Japan | 127/31 |

OTHER PUBLICATIONS

Hockett, R. C. and C. S. Hudson, "A Novel Modification of Lactose", Jour. of the Am. Chem. Society, vol. 53, Dec. 1931, pp. 4455–4456.

*Primary Examiner*—H. M. S. Sneed
*Assistant Examiner*—Chung K. Pak
*Attorney, Agent, or Firm*—David Sadowski; M. Howard Silverstein

[57] ABSTRACT

Treatment of alpha-lactose with certain alcohols ($C_1$–$C_5$) at temperature of from about 120° C. to about 160° C. and pressures of from about 500 to 200 psi for sufficient time will result in complete transformation of all forms of alpha-lactose to beta-lactose. This beta-lactose has a high solubility in water where alpha-lactose has low solubility.

5 Claims, No Drawings

PROCESS FOR CONVERTING ALPHA TO BETA-LACTOSE

BACKGROUND OF THE INVENTION

(1) Field of the Invention

This invention relates to a process for preparation of beta-lactose.

(2) Description of the Prior Art

The treatment of alpha-lactose monohydrate with various alcohols at their boiling points (at normal atmospheric pressure) led to the quantitative conversion to anhydrous alpha-lactose. This latter form of lactose does not possess the high solubility in water of beta-lactose. Subsequently, alkaline alcoholic media, at the boiling point of the alcohol, were used resulting in quantitative formation of beta-lactose. The disadvantage of this procedure is that it requires extensive washing of the beta-lactose product with alcohol in order to remove the caustic media. If the caustic media is not removed completely, the beta-lactose would not be usable, and could be harmful, in food formulations.

P. F. Sharp, U.S. Pat. No. 2,319,562, discloses a process for heating solid alpha-lactose monohydrate at temperatures of 130° C. or higher leading to the quantitative formation of a form of alpha-lactose with greater solubility in water than the lactose monohydrate. The disadvantage of this procedure is that at the temperature required to remove the water of crystallization the lactose undergoes some decomposition resulting in a brown colored product.

Beta-lactose can be produced by crystallization from an aqueous solution above 93.5° C. The disadvantages of this procedure are, that large amounts of lactose remain in the mother liquor because of the high solubility of beta-lactose in water, and residual water in the product can lead to formation of considerable amounts of alpha-lactose monohydrate.

SUMMARY OF THE INVENTION

Alpha-lactose monohydrate or anhydrous alpha-lactose is mixed with an aliphatic alcohol, and heated under pressure. The length of the time for treatment is dependent upon temperature and pressure. The mixture is allowed to cool, and the solid product, beta-lactose, is recovered quantitatively by filtration or centrifugation. The product is heated in an oven at a temperature sufficient to remove the small amounts of alcohol which adhere to the product. Converted beta-lactose thus obtained in yields of approximately 99% weight (throughout the present specification percentage refers to weight percent) is suitable for use in food products.

The main object of this invention is to provide a process for converting alpha to beta-lactose because beta-lactose is more readily soluble in water and therefore more desirable for uses in the food processing industry.

DESCRIPTION OF THE PRFERRED EMBODIMENTS

Although the process of the preferred embodiment is relatively simple, certain parameters must be observed. For an aliphatic alcohol at 120° C., the extent of conversion of alpha-lactose monohydrate to beta-lactose is 8% in 1 hour, 23% in 5 hours, and 93% in 22 hours. This rate of conversion is too slow to be of practical value. In aliphatic alcohol at 150° C., formation of beta-lactose is complete in 3 hours. Typically, the present invention utilizes, temperatures from about 120° C. to about 160° C., and pressures from about 150 to 200 psi. All forms of lactose -anhydrous lactose, amorphous (freeze-dried) lactose- any form of alpha lactose are converted to beta-lactose under these conditions. The effective aliphatic alcohol of the present invention, may for example be an aliphatic alcohol selected from the group consisting of $C_1$ to $C_5$ alcohols. Similarly, ethanol may be used instead of methanol. In all cases the final product is a pure white crystalline material having the physical properties of melting point and optical rotation identical to those of beta-lactose obtained by crystallization from water above 93.5° C. Generally, the ratio of alpha-lactose monohydrate to alcohol is 1:8 (weight basis). The use of ethyl acetate or acetone instead of methanol results in the quantitative conversion of alpha-lactose monohydrate to anhydrous alpha-lactose. Therefore, one would limit the preferred embodiment to aliphatic alcohols.

The following examples are not intended to limit the invention but are included to illustrate the preferred embodiment.

Example 1

Alpha-lactose monohydrate (50 grams) and ethanol (500 ml) ratio 1:8 (wt. basis) were stirred and heated at 150° C. in a Parr pressure vessel. The pressure developed was 180 psi. After 2 hours the conversion to beta-lactose was 52%. After 3 hours the reaction was stopped and the cooled mixture was filtered. The crystals were washed with a small volume of ethanol and dried in vacuo for 16 hours at 65° C. to give beta-lactose (47 grams, 99% of theoretical yield). The filtrate and washings were evaporated to dryness during which time crystallization occurred; the product was beta-lactose (0.5 g, 1% of theoretical yield).

Identification of the product as beta-lactose was achieved by measuring its specific optical rotation and its melting point.

Example 2

Anhydrous alpha-lactose (50 grams) was treated with ethanol (500 ml) as described in Example 1. The isolated product was beta-lactose (49.5 gms, 99% of theoretical yield).

Example 3

Alpha-lactose monohydrate was heated at 120° C. with 8 times its weight of ethanol for 1, 5, and 22 hours as described in example 1. The isolated product was examined by optical rotation which showed that the conversion to beta-lactose was 8, 23 and 93% after 1, 5 and 22 hours respectively.

Example 4

Anhydrous alpha-lactose was treated with ethanol for 22 hours at 120° C. as described in Example 3. The product was beta-lactose.

Example 5

Alpha-lactose monohydrate (2 parts) and beta-lactose (1 part) were heated at 120° C. with 8 times their weight of methanol. The product was isolated after 1 and 5 hours and revealed 51 and 95% beta-lactose respectively. Comparison of this example with Example 3 shows that the presence of added beta-lactose to the reaction mixture accelerates the overall conversion of the mixture to beta-lactose.

Example 6

Alpha-lactose monohydrate was heated at 145° C. with 8 times its weight of ethanol. After 3 hours reaction time the product was isolated and shown to be beta-lactose.

Example 7

Amorphous (freeze-dried) lactose (30 grams) was heated at 150° C. with 8 times its weight of ethanol for 3 hours. The product was beta-lactose (28 grams, 98% of theoretical yield).

Example 8

Alpha-lactose monohydrate was heated at 160° C. with 8 times its weight of ethyl acetate or acetone for 5 hours. The isolated product, obtained in quantitative yield was shown by optical rotation and melting point to be anhydrous alpha-lactose.

We claim:

1. A process for converting alpha-lactose to beta-lactose which comprise contacting said alpha lactose with an aliphatic alcohol at a temperature from about 120° C. to about 150° C. and a pressure from about 150 to 200 psi, the ratio of said alpha-lactose to said aliphatic alcohol being about 1:8.

2. The process of claim 1 wherein said aliphatic alcohol is selected from the group consisting of $C_1$ to $C_5$ alcohols.

3. The process of claim 1, wherein said aliphatic alcohol is ethanol.

4. The process of claim 1 wherein said beta-lactose is heated to remove residual quantities of alcohol.

5. The process of claim 1 wherein said contacting is carried out in the presence of beta-lactose.

* * * * *